(12) United States Patent
Clark et al.

(10) Patent No.: US 7,033,755 B2
(45) Date of Patent: Apr. 25, 2006

(54) DIAGNOSTICS AND THERAPEUTICS FOR GLAUCOMA

(75) Inventors: Abbot F. Clark, Arlington, TX (US); John Fingert, Iowa City, IA (US); Loretta McNatt, Hurst, TX (US); Edwin M. Stone, Iowa City, IA (US); Wan-Heng Wang, Grapevine, TX (US)

(73) Assignees: Alcon, Inc., Hunenberg (CH); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/796,008

(22) Filed: Feb. 28, 2001

(65) Prior Publication Data

US 2002/0049177 A1    Apr. 25, 2002

Related U.S. Application Data

(60) Provisional application No. 60/186,073, filed on Feb. 29, 2000.

(51) Int. Cl.
  C07H 21/04 (2006.01)
  C12Q 1/68 (2006.01)
(52) U.S. Cl. .................. 435/6; 435/91.1; 536/23.1
(58) Field of Classification Search .............. 435/7.1, 435/6, 91.1; 536/23.1
  See application file for complete search history.

(56) References Cited

U.S. PATENT DOCUMENTS

| | | |
|---|---|---|
| 5,798,380 A | 8/1998 | Kaufman et al. |
| 5,885,776 A | 3/1999 | Stone et al. |
| 5,916,778 A | 6/1999 | Stone et al. |
| 5,925,748 A | 7/1999 | Stone et al. |
| 5,928,662 A | 7/1999 | Phillips |
| 6,150,161 A | 11/2000 | Nguyen et al. |

FOREIGN PATENT DOCUMENTS

| | | |
|---|---|---|
| EP | 0 879 885 A1 | 11/1998 |
| EP | 0 943 684 A2 | 9/1999 |
| WO | WO 98/24932 | 6/1998 |
| WO | WO 98/42296 | 10/1998 |
| WO | WO 98/44108 | 10/1998 |
| WO | WO 98/54325 | 12/1998 |
| WO | WO 99/09152 | 2/1999 |
| WO | WO 99/42481 | 8/1999 |
| WO | WO 00/07565 | 2/2000 |
| WO | WO 01/19855 | 9/2000 |

OTHER PUBLICATIONS

Trevor C. Dale, BIOCHEM. J. (1998) pp. 209-229.*
Randall T. Moon et al., SCIENCE, May 31, 2002, vol. 296, pp. 1644-1646.*
Tayebeh Rezaie et al., SCIENCE, Feb. 8, 2002, vol. 295, pp. 1077-1079.*

Huelsken, J. et al. New Aspects of Wnt signaling pathways in higher vertebrates. Current Opinion in Genetics & Development 2001, vol. 11, No. 5, pp. 547-553.*
Zhou et al. (1998), *Up-Regulation of Human Secreted Frizzled Homolog in Apoptosis and Its Down-Regulation in Breast Tumors*, Int. J. Cancer 78:95.
Dale (1998), *Signal Transduction by the Wnt Family of Ligands*, BIOCHEM. J. 329:209.
Brown et al. (1998), *Wnt Signaling: Why is Everything so Negative?*, Curr. Opin. in Cell Biol. 10:182.
Clark et al. (1995), *Cytoskeletal Chages in Cultured Human Glaucoma Trabecular Meshwork Cells*, J. Glaucoma 4:183.
Wilson et al. (1993), *Dexamethasone Induced Ultrastructural Changes in Cultures Human Trabecular Meshwork Cells*, Curr. Eye Res. 12:783.
Clark et al. (1996), *Inhibition of Dexamethasone-Induced Cytoskeletal Changes in Cultural Human Trabecular Meshwork Cells by Tetrahydrocortisol*, Invest. Ophthal. & Visual Science 37(5):805.
Wordinger et al. (1998), *Cultured Human Trabecular Meshwork Cells Express Functional Growth Factor Receptors*, Invest. Ophthal. & Visual Science 39(9):1575.
Steely et al. (2000), *The Similarity of Protein Expression in Trabecular Meshwork and Lamina Cribrosa: Implications for Glaucoma*, Exp. Eye Res. 70:17.
Wilder et al. (1995), *Dual Funcations of Wingless in the Drosophila Leg Imaginal Disc*, Development 121:477.
Dennis et al. (1999), *A Secreted Frizzled Related Protein, FrzA, Selectively Associates with Wnt-I Protein and Regulates Wnt-I Signaling*, J. Cell Sci. 112:3815.
Chang et al. (1999), *Cloning and Characterization of a Secreted Frizzled-Related Protein That is Expressed by the Retinal Pigment Epithelium*, Human Molcular Genetics 8 (4):575.
Jasoni et al. (1999), *Analysis of Chicken Wnt-13 Expression Demonstrates Coincidence with Cell Division in the Developing Eye and is Consistent with a role in Induction*, Develop. Dynamics 215:215.
Deardorff et al. (1999), *Xenopus Frizzled-2 is Expressed Highly in the Developing Eye, Otic Vesicle and Somites*, Mechanisms of Development 87:229.
Craig et al.; "Glaucoma Genetics: Where are we? Where will we go?", Current Opinion in Ophthalmology 10: 126-134, (1999.
International Search Report Completed on Jun. 13, 2002 and Mailed on Jun. 26, 2002.
Office Action issued by European Patent Office in corresponding European Application No. 01 913 057.4-1222 dated Aug. 5, 2005.
Miller, et al., "Mechanism and Function of Signal Transduction by the Wnt/$\beta$-Catenin and Wnt/$Ca^{2+}$ Pathways," Oncogene, vol. 18, Dec. 20, 1999, pp. 7860-7872.

(Continued)

*Primary Examiner*—Anne-Marie Falk
*Assistant Examiner*—Jon Eric Angell
(74) *Attorney, Agent, or Firm*—Kilyk & Bowersox, P.L.L.C.

(57) ABSTRACT

Methods and compositions for diagnosing and treating glaucoma are disclosed.

3 Claims, 4 Drawing Sheets

OTHER PUBLICATIONS

Nusse, "Model of Wnt Signaling," Jul. 2005, retrieved from internet URL:http://www.stanford.edu/~musse/pathways/cell2-html.

"Wnt Complex," Jul. 2005, retrieved from Internet: URL: http://www.em2.molmed.uni-erlangen.de/pics/Wnt_complex_highQ/jpg>.

* cited by examiner

```
   1    cctgcagcct ccggagtcag tgccgcgcgc ccgccgcccc gcgccttcct gctcgccgca
  61    cctccgggag ccggggcgca cccagcccgc agcgccgcct ccccgcccgc gccgcctccg
 121    accgcaggcc gagggccgcc actggccggg gggaccgggc agcagcttgc ggccgcggag
 181    ccgggcaacg ctggggactg cgccttttgt ccccggaggt ccctggaagt ttgcggcagg
 241    acgcgcgcgg ggaggcggcg gaggcagccc cgacgtcgcg gagaacaggg cgcagagccg
 301    gcatgggcat cgggcgcagc gagggggggcc gccgcggggc cctgggcgtg ctgctggcgc
 361    tgggcgcggc gcttctggcc gtgggctcgg ccagcgagta cgactacgtg agcttccagt
 421    cggacatcgg cccgtaccag agcgggcgct tctacaccaa gccacctcag tgcgtggaca
 481    tccccgcgga cctgcggctg tgccacaacg tgggctacaa gaagatggtg ctgcccaacc
 541    tgctggagca cgagaccatg gcggaggtga agcagcaggc cagcagctgg gtgcccctgc
 601    tcaacaagaa ctgccacgcc gggacccagg tcttcctctg ctcgctcttc gcgcccgtct
 661    gcctggaccg gcccatctac ccgtgtcgct ggctctgcga ggccgtgcgc gactcgtgcg
 721    agccggtcat gcagttcttc ggcttctact ggcccgagat gcttaagtgt gacaagttcc
 781    cggaggggga cgtctgcatc gccatgacgc cgcccaatgc caccgaagcc tccaagcccc
 841    aaggcacaac ggtgtgtcct ccctgtgaca acgagttgaa atctgaggcc atcattgaac
 901    atctctgtgc cagcgagttt gcactgagga tgaaaataaa agaagtgaaa aaagaaaatg
 961    gcgacaagaa gattgtcccc aagaagaaga agccctgaa gttggggccc atcaagaaga
1021    aggacctgaa gaagcttgtg ctgtacctga agaatggggc tgactgtccc tgccaccagc
1081    tggacaacct cagccaccac ttcctcatca tgggccgcaa ggtgaagagc cagtacttgc
1141    tgacggccat ccacaagtgg gacaagaaaa acaaggagtt caaaaacttc atgaagaaaa
1201    tgaaaaacca tgagtgcccc acctttcagt ccgtgtttaa gtgattctcc cggggggcagg
1261    gtggggaggg agcctcgggt ggggtgggag cgggggggac agtgcccggg aacccgtggt
1321    cacacacacg cactgccctg tcagtagtgg acattgtaat ccagtcggct tgttcttgca
1381    gcattcccgc tccctttccc tccatagcca cgctccaaac cccagggtag ccatggccgg
1441    gtaaagcaag ggccatttag attaggaagg tttttaagat ccgcaatgtg gagcagcagc
1501    cactgcacag gaggaggtga caaaccattt ccaacagcaa cacagccact aaaacacaaa
1561    aagggggatt gggcggaaag tgagagccag cagcaaaaac tacattttgc aacttgttgg
1621    tgtggatcta ttggctgatc tatgccttte aactagaaaa ttctaatgat tggcaagtca
1681    cgttgttttc aggtccagag tagtttcttt ctgtctgctt taaatggaaa cagactcata
1741    ccacacttac aattaaggtc aagcccagaa agtgataagt gcagggagga aaagtgcaag
1801    tccattatct aatagtgaca gcaagggac caggggagag gcattgcctt ctctgcccac
1861    agtctttccg tgtgattgtc tttgaatctg aatcagccag tctcagatgc cccaaagttt
1921    cggttcctat gagcccgggg catgatctga tccccaagac atgtggaggg gcagcctgtg
1981    cctgcctttg tgtcagaaaa aggaaaccac agtgagcctg agagagacgg cgatttcgg
2041    gctgagaagg cagtagtttt caaaacacat agttaaaaaa gaaacaaatg aaaaaaattt
2101    tagaacagtc cagcaaattg ctagtcaggg tgaattgtga aattgggtga agagcttagg
2161    attctaatct catgtttttt ccttttcaca tttttaaaag aacaatgaca acacccact
2221    tatttttcaa ggttttaaaa cagtctacat tgagcatttg aaaggtgtgc tagaacaagg
2281    tctcctgatc cgtccgaggc tgcttcccag aggagcagct ctccccaggc atttgccaag
2341    ggaggcggat ttccctggta gtgtagctgt gtggctttcc ttcctgaaga gtccgtggtt
2401    gccctagaac ctaacacccc ctagcaaaac tcacagagct ttccgttttt ttctttcctg
2461    taaagaaaca tttcctttga acttgattgc ctatggatca aagaaattca gaacagcctg
2521    cctgttcccc cgcactttt acatatattt gtttcatttc tgcagatgga aagttgacat
2581    gggtggggtg tccccatcca gcgagagagt ttcaaaagca aaacatctct gcagtttttc
2641    ccaagtaccc tgagatactt cccaaagccc ttatgtttaa tcagcgatgt atataagcca
2701    gttcacttag acaactttac ccttcttgtc caatgtacag gaagtagttc taaaaaaaat
2761    gcatattaat ttcttccccc aaagccggat tcttaattct ctgcaacact ttgaggacat
2821    ttatgattgt ccctctgggc caatgcttat acccagtgag gatgctgcag tgaggctgta
2881    aagtggcccc ctgcggccct agcctgaccc ggagaaagga tggtagattc tgttaactct
2941    tgaagactcc agtatgaaaa tcagcatgcc cgcctagtta cctaccggag agttatcctg
3001    ataaattaac ctctcacagt tagtgatcct gtcctttaa cacctttttt gtggggttct
3061    ctctgacctt tcatcgtaaa gtgctgggga ccttaagtga tttgcctgta attttggatg
3121    attaaaaaat gtgtatatat attagctaat tagaaatatt ctacttctct gttgtcaaac
3181    tgaaattcag agcaagttcc tgagtgcgtg gatctgggtc ttagttctgg ttgattcact
```

FIGURE 1

```
3241  caagagttca gtgctcatac gtatctgctc attttgacaa agtgcctcat gcaaccgggc
3301  cctctctctg cggcagagtc cttagtggag gggtttacct ggaacataag tagttaccac
3361  agaatacgga agagcaggtg actgtgctgt gcagctctct aaatgggaat tctcaggtag
3421  gaagcaacag cttcagaaag agctcaaaat aaattggaaa tgtgaatcgc agctgtgggt
3481  tttaccaccg tctgtctcag agtcccagga ccttgagtgt cattagttac tttattgaag
3541  gttttagacc catagcagct ttgtctctgt cacatcagca atttcagaac caaaagggag
3601  gctctctgta ggcacagagc tgcactatca cgagcctttg tttttctcca caaagtatct
3661  aacaaaacca atgtgcagac tgattggcct ggtcattggt ctccgagaga ggaggtttgc
3721  ctgtgatttg cctgtgattt cctaattatc gctagggcca aggtgggatt tgtaaagctt
3781  tacaataatc attctggata gagtcctggg aggtccttgg cagaactcag ttaaatcttt
3841  gaagaatatt tgtagttatc ttagaagata gcatgggagg tgaggattcc aaaaacattt
3901  tatttttaaa atatcctgtg taacacttgg ctcttggtac ctgtgggtta gcatcaagtt
3961  ctccccaggg tagaattcaa tcagagctcc agtttgcatt tggatgtgta aattacagta
4021  atcccatttc ccaaacctaa aatctgtttt tctcatcaga ctctgagtaa ctggttgctg
4081  tgtcataact tcatagatgc aggaggctca ggtgatctgt ttgaggagag caccctaggc
4141  agcctgcagg gaataacata ctggccgttc tgacctgttg ccagcagata cacaggacat
4201  ggatgaaatt cccgtttcct ctagtttctt cctgtagtac tcctctttta gatcctaagt
4261  ctcttacaaa agctttgaat actgtgaaaa tgttttacat tccatttcat ttgtgttgtt
4321  tttttaactg cattttacca gatgttttga tgttatcgct tatgttaata gtaattcccg
4381  tacgtgttca ttttattttc atgctttttc agccatgtat caatattcac ttgactaaaa
4441  tcactcaatt aatcaatgaa aaaaaaaa
```

FIGURE 1 (con't)

FRP amino acid sequence

Met Gly Ile Gly Arg Ser Glu Gly Gly Arg Arg Gly Ala Leu Gly Val Leu Leu
Ala Leu Gly Ala Ala Leu Leu Ala Val Gly Ser Ala Ser Glu Tyr Asp Tyr Val
Ser Phe Gln Ser Asp Ile Gly Pro Tyr Gln Ser Gly Arg Phe Tyr Thr Lys Pro
Pro Gln Cys Val Asp Ile Pro Ala Asp Leu Arg Leu Cys His Asn Val Gly Tyr
Lys Lys Met Val Leu Pro Asn Leu Leu Glu His Glu Thr Met Ala Glu Val Lys
Gln Gln Ala Ser Ser Trp Val Pro Leu Leu Asn Lys Asn Cys His Ala Gly Thr
Gln Val Phe Leu Cys Ser Leu Phe Ala Pro Val Cys Leu Asp Arg Pro Ile Tyr
Pro Cys Arg Trp Leu Cys Glu Ala Val Arg Asp Ser Cys Glu Pro Val Met Gln
Phe Phe Gly Phe Tyr Trp Pro Glu Met Leu Lys Cys Asp Lys Phe Pro Glu Gly
Asp Val Cys Ile Ala Met Thr Pro Pro Asn Ala Thr Glu Ala Ser Lys Pro Gln
Gly Thr Thr Val Cys Pro Pro Cys Asp Asn Glu Leu Lys Ser Glu Ala Ile Ile
Glu His Leu Cys Ala Ser Glu Phe Ala Leu Arg Met Lys Ile Lys Glu Val Lys
Lys Glu Asn Gly Asp Lys Lys Ile Val Pro Lys Lys Lys Pro Leu Lys Leu
Gly Pro Ile Lys Lys Lys Asp Leu Lys Lys Leu Val Leu Tyr Leu Lys Asn Gly
Ala Asp Cys Pro Cys His Gln Leu Asp Asn Leu Ser His His Phe Leu Ile Met
Gly Arg Lys Val Lys Ser Gln Tyr Leu Leu Thr Ala Ile His Lys Trp Asp Lys
Lys Asn Lys Glu Phe Lys Asn Phe Met Lys Lys Met Lys Asn His Glu Cys Pro
Thr Phe Gln Ser Val Phe Lys ***

FIGURE 2

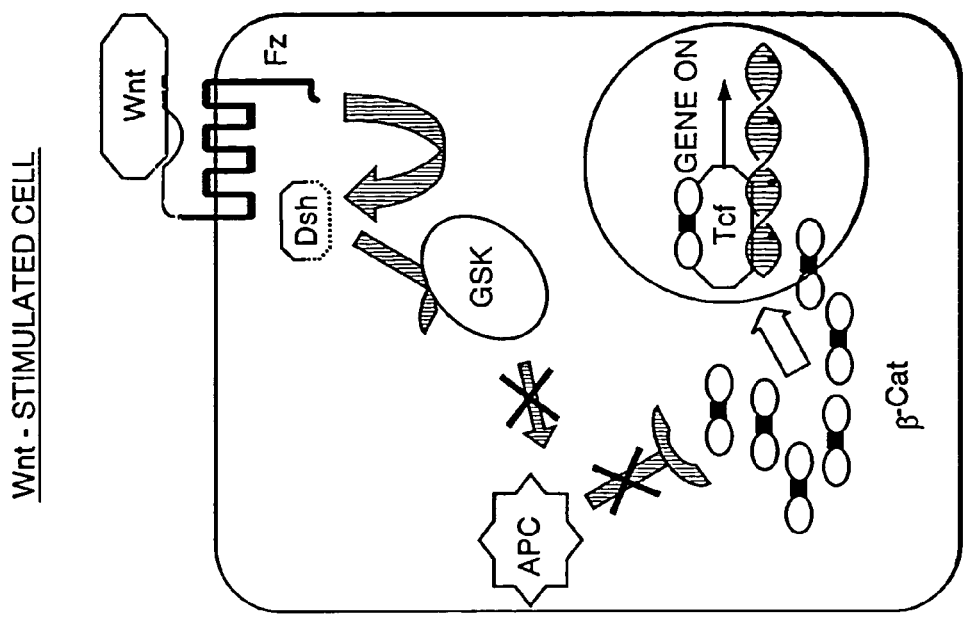
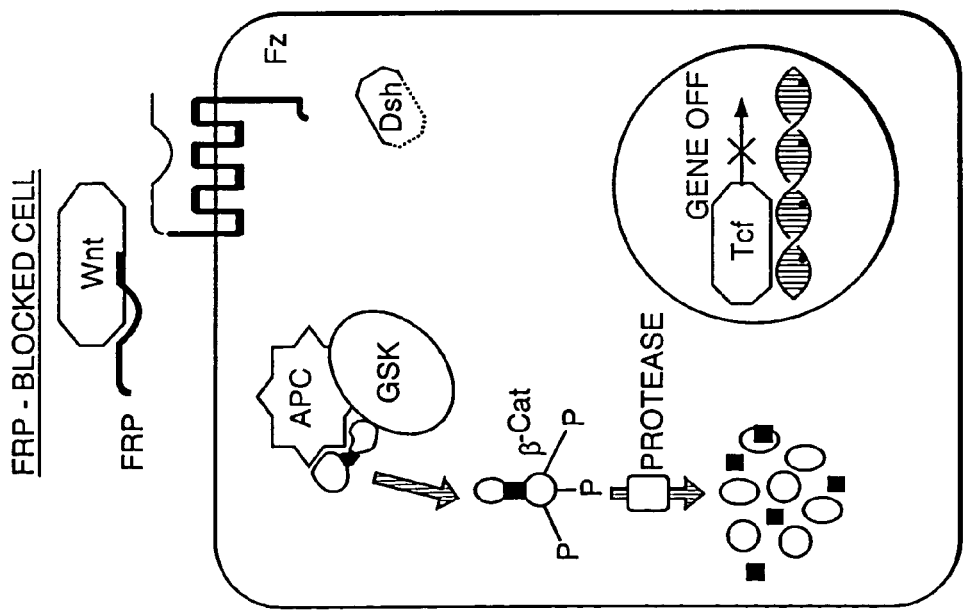
FIGURE 3

DIAGNOSTICS AND THERAPEUTICS FOR GLAUCOMA

RELATED APPLICATIONS

This application claims priority to U.S. Provisional Application No. 60/186,073, filed 29 Feb. 2000, the entire contents of which are incorporated herein by reference.

1. BACKGROUND OF THE INVENTION

Glaucoma

Glaucoma is a group of ocular disorders, characterized by degeneration of the optic nerve. It is one of the leading causes of blindness worldwide. One major risk factor for developing glaucoma is family history. Several different inherited forms of glaucoma have been described.

Primary congenital or infantile glaucoma is an inherited disorder that is characterized by an improper development of the aqueous outflow system of the eye, which leads to elevated intraocular pressure, enlargement of the glove or cornea (i.e., buphthalmos), damage to the optic nerve, and eventual visual impairment.

Primary open angle glaucoma (POAG) is a common disorder characterized by atrophy of the optic nerve resulting in visual field loss and eventual blindness. POAG has been divided into two major groups, based on age of onset and differences in clinical presentation. Juvenile-onset POAG usually manifests itself in late childhood or early adulthood. Its progression is rapid and severe, with high intraocular pressure. This type of POAG is poorly responsive to medical treatment, and usually requires ocular surgery. Adult- or late-onset POAG is the most common type of glaucoma. It is milder and develops more gradually than juvenile-onset POAG, with variable onset usually after the age of 40. This type of POAG is associated with slight to moderate elevation of intraocular pressure, and often responds satisfactorily to regularly monitored medical treatment. Unfortunately, this disease may not be detected until after irreversible damage to the optic nerve has already occurred because it progresses gradually and painlessly.

Both types of POAG are often associated with elevated intraocular pressure as a result of an inhibition of aqueous humor outflow through the trabecular meshwork. The pathophysiology of the human trabecular meshwork (HTM) in POAG has been characterized by an increase in extracellular matrix components and a decrease in the number of trabecular meshwork cells. It is thus probable that a defect in the structure, function or number of HTM cells influences the pathogenesis of POAG. The pathophysiology of POAG also involves the cells of the human lamina cribrosa (HLC), which has been shown to possess a pattern of protein expression that is similar to the HTM (Steely et al. (2000) Exp Eye Res 70: 17–30). Accordingly, POAG may have a common causal origin in the two tissues most responsible for damage to the neural retina. Therefore, it will be important to identify and understand the cellular control mechanisms acting within the HTM and the HLC in order to both understand the molecular etiology of POAG and identify unique treatment modalities.

Cultured HTM cells have been shown to express mRNA for numerous growth factor receptors and, furthermore, these expressed receptors have been shown to be functional because exogenous growth factor administration elicits a physiologic response (Wordinger et al. (1998) Invest Ophthalmol Vis Sci 39: 1575–89). In vivo, these receptors may be activated by growth factors present within the aqueous humor (aquecrine/paracrine) or by growth factors synthesized and released locally by trabecular meshwork cells themselves (autocrine). Indeed, TGF-b isoforms have been shown to significantly inhibit EGF-stimulated trabecular meshwork cell proliferation, while FGF-1, TGF-a, EGF, IL-1a, Il-1b, HGF, TNF-a, PDGF-AA, and IGF-1 significantly stimulated extracellular acidification (ibid.). Specific growth factors acting through high-affinity receptors may be involved in maintaining the normal microenvironment of the HTM and also may be involved in the pathogenesis of POAG.

One insight into the molecular pathology comes from the observation that glucocorticoids, which can induce ocular hypertension in both animals and humans, alter the cytoskeletal structure of cultured HTM cells (Wilson et al. (1993) Current Eye Res 12: 783–93). These cytoskeletal changes involve the reorganization of actin microfilaments into cross-linked actin networks (CLANs), and this structural alteration may be the ultimate physiological change which brings about ocular hypertension (Clark et al. (1993) J Glaucoma 4: 183–88). Indeed, the hypotensive steroid tetrahydrocortisol, which has been shown to lower the intraocular pressure (IOP) of glucocorticoid-induced ocular hypertension, also appears to inhibit these glucocorticoid-mediated changes in the HTM cytoskeleton (Clark et al. (1996) Inv Ophthal & Vis Sci 37: 805–813).

U.S. Pat. Nos. 5,925,748, 5,916,778 and 5,885,776 disclose diagnostic methods for glaucoma associated with mutations in the GLC1A gene and assays for identifying glaucoma therapeutics that modulate the activity of the MYOC protein encoded by the GLC1A gene. The Wnt signaling pathway.

The Wnt gene family encodes secreted ligand proteins that serve key roles in differentiation and development. This family comprises at least 15 vertebrate and invertebrate genes including the *Drosophila* segment polarity gene wingless and one of its vertebrate homologues, integrated from which the Wnt name derives. The Wnt proteins appear to facilitate a number of developmental and homeostatic processes. For example, vertebrate Wnt1 appears to be active in inducing myotome formation within the somites and in establishing the boundaries of the midbrain (see McMahon and Bradley (1990) Cell 62: 1073; Ku and Melton (1993) Development 119: 1161; Stern et al. (1995) Development 121: 3675). During mammalian gastrulation, Wnt3a, Wnt5a, and Wnt5b are expressed in distinct yet overlapping regions within the primitive streak. Wnt3a is the only Wnt protein seen in the regions of the streak that will generate the dorsal (somite) mesoderm, and mice homozygous for a null allele of the Wnt3a gene have no somites caudal to the forelimbs. The Wnt genes also are important in establishing the polarity of vertebrate limbs, just as the invertebrate homolog wingless has been shown to establish polarity during insect limb development. In both cases there are interactions with Hedgehog family members as well.

The Wnt signaling pathway comprises a number of proteins involved in the transduction of Wnt/wingless signaling and is intimately connected to the hedgehog developmental pathway. In *Drosophila*, the secreted wingless protein mediates reciprocal interaction between cells in the wingless-hedgehog pathway by binding to neighboring cells through the Frizzled receptor. The Frizzled receptor then activates Dishelveled protein, which blocks the inhibiting action of Zeste-white-3 kinase upon the Armadillo protein (a beta-catenin protein). The active Armadillo protein, acts with the high mobility group (HMG) protein LEF/TCF (Lymphoid Enhancer Factor/T-Cell Factor) to promote nuclear expression of the hedgehog (hh) gene. Hedgehog is a secreted protein which can bind to cells adjacent to the Wnt/wingless-activated cell through another receptor, the Patched protein. Binding of the Hedgehog protein to the Patched receptor activates nuclear expression of the wingless protein, which is then secreted and further reinforces the reciprocal signaling with the neighboring hedgehog-secreting cell. The Wnt/Wingless-Hedgehog reciprocal signaling system thereby facilitates the differential determination of two adjacent cells during vertebrate and invertebrate development. This results in the stabilization of a differentiated border wherein the tissue on one side secretes Hedgehog protein, while the tissue on the other side produces Wingless. Indeed, the cell surface plays an extremely critical role in development and homeostasis by effecting the differential adhesion of one cell to another, as well as to an extracellular matrix. Furthermore, once differential cell adhesion has occurred, the action of Wnt/Wingless-Hedgehog processes facilitates the continued signaling between adjacent cell layers.

This Wnt/Wingless border is critical in the production of segments and appendages in *Drosophila* as well as brain and limb subdivisions in the mammals (Ingham (1994) Curr Biol 4: 1; Niswander et al. (1994) Nature 371: 609; Wilder and Perrimon (1995) Development 121: 477). In *Xenopus*, frizzled-2 receptor (xfz2) is highly expressed following gastrulation in the eye anlage and otic vesicle (Deardorff and Klein (1999) Mech Dev 87: 229), and in chicken, a particular Wnt gene family member, Wnt13, has been shown to be expressed in the proliferative epithelium of the lens and both pigmented and non-pigmented layers of the ciliary margin (Jasoni et al. (1999) Dev Dyn 215: 215). The reciprocal Wnt/Wingless-Hedgehog pathway may also play a role in the maintenance of normal differentiated somatic tissue. For example, in human, sporadic loss-of-function mutations of the patched gene in somatic tissues causes basal cell carcinomas, the most common type of human cancer. Furthermore, heritable mutations of the patched gene give rise to basal cell nevus syndrome, an autosomal dominant condition characterized by developmental abnormalities, including rib and craniofacial alterations, and malignant tumors (Hahn et al. (1996) Cell 85: 841; Johnson et al. (1996) Science 272: 1668).

Recently a protein homologous to mammalian Wnt receptor Frizzled, termed the secreted or soluble frizzled related protein 5 (SFRP5) has been shown to be preferentially expressed by the vertebrate retinal pigment epithelium (RPE) (Chang et al. (1999) Hum Mol Genet 8: 575). Furthermore, another SFRP, SPRP2 has been shown to be expressed specifically by cells of the inner nuclear layer. As a result, photoreceptor cells of the retina are exposed to two opposing gradients of SFRP molecules. Because the frizzled related proteins do not contain a membrane spanning domain, they are thought to be a secreted, soluble form of the receptor which interferes with Wnt signaling through the normal seven transmembrane Frizzled receptor. Indeed, FrzA, an sFRP that is highly expressed in vascular endothelium and a variety of epithelium, specifically binds to Wnt-1 protein and thereby blocks Wnt-1 signaling through the Frizzled receptor (Dennis et al. (1999) J Cell Sci 112: 3815).

2. SUMMARY OF THE INVENTION

In one aspect, the present invention provides novel methods and kits for determining whether a subject has or is predisposed to developing glaucoma. In one embodiment, the method is based on determining the relative level or activity of a Frizzle Related Protein (FRP), a wingless (Wnt) signaling pathway component, a gene activated by Wnt signaling or the gene product of a gene activated by Wnt signaling. In preferred embodiments, the assay is performed on trabecular meshwork cells obtained from a subject. The method can include detecting in appropriate cells, the presence or absence of a genetic lesion characterized by at least one of: (i) a mutation of a gene encoding Frizzle Related Protein (FRP-1), a Wnt signaling component or a gene whose expression is activated by Wnt signaling; (ii) the misexpression of FRP, a Wnt signaling component or a gene whose expression is activated by Wnt signaling; or (iii) an error or mutation in the promoter regulating FRP, a Wnt signaling component or a gene whose expression is activated by Wnt signaling, said error or mutation leading to aberrant expression.

In particularly preferred embodiments, the diagnostic methods comprise ascertaining the existence of at least one of (a) a deletion of one or more nucleotides from a wildtype FRP, Wnt signaling component or a gene whose expression is activated by Wnt signaling; (b) an addition of one or more nucleotides to a wildtype FRP, Wnt signaling component or a gene whose expression is activated by Wnt signaling; (c) a substitution of one or more nucleotides of a wildtype FRP, Wnt signaling component or a gene whose expression is activated by Wnt signaling; (d) a gross chromosomal rearrangement of a wildtype FRP, Wnt signaling component or a gene whose expression is activated by Wnt signaling; (e) an alteration in the level of a messenger RNA (mRNA) transcript of a FRP, Wnt signaling component or a gene whose expression is activated by Wnt signaling; (f) the presence of a non-wildtype splicing pattern of a mRNA transcript of an FRP, Wnt signaling component or a gene whose expression is activated by Wnt signaling; (g) an aberrant level or activity of an FRP, Wnt signaling protein or a protein encoded by a gene whose expression is activated by Wnt signaling.

For example, a genetic lesion can be detected by: (i) providing probes and primers comprised of an oligonucleotide, which hybridizes to a sense or antisense sequence of an FRP, Wnt signaling component or a gene whose expression is activated by Wnt signaling (wildtype or mutant) or fragment thereof or 5' or 3' flanking sequence naturally associated with an FRP, Wnt signaling component or a gene whose expression is activated by Wnt signaling; (ii) contacting the probes or primers to an appropriate nucleic acid containing biological sample obtained from the subject; and (iii) detecting, by hybridization of the probes or primers to the nucleic acid, the presence or absence of the genetic lesion. In a preferred embodiment, the diagnostic methods and/or kits utilize a set of primers for amplifying (e.g. via PCR or LCR) at least one region of an FRP, Wnt signaling component or a gene whose expression is activated by Wnt signaling that may contain a mutation, and means for analyzing the amplification product for differences mutations or gene expression levels from the normal, wildtype coding sequence. In another preferred embodiment, the diagnostic methods and/or kits utilize a probe to determine its ability to hybridize under appropriately stringent conditions to a complementary nucleic acid sequence in the biological sample, wherein an inability of a probe, which is comprised of a wildtype FRP, Wnt signaling component or a gene whose expression is activated by Wnt signaling, to hybridize to the sample nucleic acid is indicative of the presence of a mutation in the sample nucleic acid; or the ability of a probe which is comprised of a mutant FRP, Wnt signaling component or a gene whose expression is activated by Wnt signaling, to hybridize to the sample nucleic acid is indicative of the presence of a mutation in the sample nucleic acid. In another preferred embodiment, the protein level or activity of an FRP, Wnt signaling component or a protein encoded by a gene whose expression is activated by Wnt signaling can be detected using any of a variety of methods, including immunodetection and biochemical tests.

Information obtained using the assays and kits described herein (alone or in conjunction with information on another genetic defect or environmental factor, which contributes to the development of glaucoma) is useful for determining whether a non-symptomatic subject has or is likely to develop glaucoma. In addition, the information can allow a more customized approach to the prevention or treatment of the disorder.

In another aspect, the invention provides in vitro or in vivo assays for screening test compounds to identify therapeutics for treating or preventing glaucoma. In particularly preferred embodiments, the therapeutics promote Wnt signaling. In one embodiment, the method is a binding assay, which consists essentially of the steps of (a) forming a reaction mixture, including: (i) an FRP or Wnt signaling polypeptide, (ii) an FRP or Wnt signaling polypeptide binding partner, and (iii) a test compound and (b) detecting interaction of the FRP or Wnt signaling polypeptide and the binding protein. A statistically significant change (potentiation or inhibition) in the interaction of the FRP or Wnt signaling polypeptide and the binding protein in the presence of the compound, indicates a potential agonist (mimetic or potentiator) or antagonist (inhibitor) of Wnt signaling. The reaction mixture can be a cell-free protein preparation, e.g. a reconstituted protein mixture or a cell lysate, a cultured cell system, or it can be a recombinant cell including a heterologous nucleic acid recombinantly expressing the binding partner.

Yet another exemplary embodiment provides an assay for screening test compounds to identify agents which promote or increase the rate of Wnt signaling and/or expression of genes, which are regulated by Wnt signaling in the trabecular meshwork. In one embodiment, the screening assay comprises contacting a cell transfected with a reporter gene operably linked to a promoter, which is regulated by a high mobility group (HMG) protein (e.g. Lymphoid Enhancer Factor/T-Cell Factor) with a test compound and determining the level of expression of the reporter gene. The reporter gene can encode, e.g., a gene product that gives rise to a detectable signal such as: color, fluorescence, luminescence, cell viability, relief of a cell nutritional requirement, cell growth, and drug resistance. For example, the reporter gene can encode a gene product selected from the group consisting of chloramphenicol acetyl transferase, luciferase, beta-galactosidase and alkaline phosphatase.

In a further aspect, the invention features methods for treating glaucoma by contacting appropriate cells (e.g. trabecular meshwork cells) with an effective amount of a compound that promotes the expression of trabecular meshwork genes that are involved in or are regulated by Wnt signaling. Preferred compounds can be small molecules, nucleic acids (including antisense or triplex molecules and ribozymes), proteins, peptides or peptide mimetics. Particularly preferred compounds are Frizzle Related Protein (FRP) antagonists. Particularly preferred antagonists are antisense, ribozyme or triplex molecules that inhibit or decrease the level of FRP expressed in cells. Other preferred FRP antagonists are antibodies, which reduce or inhibit FRP binding to Wnt.

Other features and advantages of the invention will be apparent from the following detailed description and claims.

3. BRIEF DESCRIPTION OF THE FIGURES

FIG. 1 shows the cDNA sequence of human Frizzle Related Protein (FRP1) (SEQ ID NO: 1).

FIG. 2 shows the amino acid sequence of the human FRP-1 (SEQ ID NO: 2).

FIG. 3 schematically depicts the Wnt signal transduction pathway.

FIG. 3(a) shows the inhibition of gene expression based on binding of FRP to Wnt.

FIG. 3(b) shows Wnt stimulated gene expression. The binding of Wnt to a frizzled protein (Fz) activates disheveled (Dsh) which in turn prevents the binding of glycogen-synthase-kinase 3 (GSK3) to protein kinase C (APC), which results in the accumulation of β-catenin, which in turn facilitates interactions with the transcription factor, T cell factor (TCF), promoting gene expression.

4. DETAILED DESCRIPTION OF THE INVENTION

4.1. General

In general, the invention is based on the finding that frizzled related protein-1 (FRP-1) is upregulated in the trabecular meshwork (TM) of glaucoma patients. Although not wishing to be bound, it is thought that the Wnt signaling pathway works in the TM as depicted in FIG. 3(b) to regulate important trabecular meshwork cell functions and that FRP-1 antagonizes normal Wnt signaling, as shown in FIG. 3(a), thereby interfering with TM cell function.

4.2 Definitions

For convenience, the meaning of certain terms and phrases employed in the specification, examples, and appended claims are provided below.

The term "aberrant", as used herein is meant to refer to an alteration in a gene product level or bioactivity which is found in a glaucomatous tissue or cells but not in a non-glaucomatous tissue or cells. For example, an aberrantly high level of frizzle related protein gene product is associated with glaucomatous trabecular meshwork cells obtained from a glaucoma patient than from nonglaucomatous trabecular meshwork cells obtained from a normal patient. Furthermore, an aberrantly low bioactivity of Wnt pathway components is associated with trabecular meshwork cells from a normal patient.

The term "an aberrant activity", as applied to an activity of a polypeptide such as FRP, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant FRP activity due to overexpression or underexpression of the gene encoding FRP.

The term "agonist", as used herein, is meant to refer to an agent that directly or indirectly enhances, supplements or potentiates Wnt initiated gene expression or the level or activity of a protein encoded by a Wnt regulated gene or a gene or protein in the Wnt signaling pathway.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The term "antagonist", as used herein, is refers to an agent that directly or indirectly prevents, minimizes or suppresses Wnt initiated gene expression or the level or activity of a protein encoded by a Wnt regulated gene or a gene or protein in the Wnt signaling pathway.

The term "binding partner", as used herein refers to a composition of matter that interacts though noncolavent forces with a specified gene product. For example, "binding partners" of the frizzled related protein gene product include compositions of matter which interact with frizzled related protein gene mRNAs, such as an FRP-1 antisense polynucleotide, and compositions which interact with frizzled related protein polypeptides, such as Wnt polypeptides.

As used herein the term "bioactive fragment of a polypeptide" refers to a fragment of a full-length polypeptide, wherein the fragment specifically mimics or antagonizes an activity of the corresponding full-length wild-type polypeptide.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding, for example, one of the subject FRP polypeptides with a second amino acid sequence defining a domain (e.g. polypeptide portion) foreign to and not substantially homologous with any domain of an FRP polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula X-FRP-Y, wherein FRP represents a portion of the polypeptide which is derived from an FRP polypeptide, and X and Y are independently absent or represent amino acid sequences which are not related to an FRP sequence in an organism, including naturally occurring mutants.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes may exist in single or multiple copies within the genome of an individual. Such duplicate genes may be identical or may have certain modifications, including nucleotide substitutions, additions, inversions or deletions, which all still code for polypeptides having substantially the same activity. The term "DNA sequence encoding an FRP polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

A "Frizzled Related Protein (FRP)" can be any member of a family of secreted proteins with similarity to the extracellular, ligand-binding domain of Frizzled proteins. FRPs are also referred to as secreted or soluble frizzled-related protein (sFRPs) because they do not contain a membrane spanning domain and hence appear to act as dominant-negative receptors of Wnt proteins. FRPs are encoded by a number of different vertebrate genes including: the human secreted frizzled-related protein encoding gene Frz-1 (GenBank Accession No. AF056087); the human secreted frizzled-related protein encoding gene SFRP5 (GenBank Accession No. AF117758); the human FrzB gene (GenBank Accession No. U24163); and the *Xenopus* FrzA gene (Genbank Accession No. AF049908).

The term "glaucoma", as used herein refers to a group of eye diseases characterized by characteristic degeneration of the optic nerve head and visual field loss, which is often caused by increased intraocular pressure due to blockage of the channel through which aqueous humor drains (chronic or open-angle glaucoma) or by pressure of the iris against the lens (acute or angle-closure glaucoma).

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. The percentage homology between two nucleic acid or polypeptide sequence can be determined using any of several mathematical algorithms which are well known in the art (as provided, for example, by the BLAST sequence homology software available online from the National Center for Biotechnology Information, National Library of Medicine, National Institutes of Health, Bethesda, Md. An "unrelated" or "non-homologous" sequence shares less than 40% identity, though preferably less than 25% identity, with one of the FRP sequences of the present invention.

The term "interact" as used herein is meant to include detectable interactions between molecules, such as can be detected using, for example, a yeast two hybrid assay. The term interact is also meant to include "binding" interactions between molecules. Interactions may, for example, be protein-protein or protein-nucleic acid or nucleic acid-nucleic acid in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject FRP polypeptides preferably includes no more than 10 kilobases (kb) of nucleic acid sequence which naturally immediately flanks the FRP gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammals such as rodents, non-human primates, sheep, dogs, cows, chickens, amphibians, reptiles, rabbits, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO. x refers to the complementary strand of the strand having SEQ ID NO. x or to any nucleic acid having the nucleotide sequence of the complementary strand of SEQ ID NO. x. When referring to a single stranded nucleic acid having the nucleotide sequence SEQ ID NO. x, the complement of this nucleic acid is a nucleic acid having a nucleotide sequence which is complementary to that of SEQ ID NO. x. The nucleotide sequences and complementary sequences thereof are always given in the 5' to 3' direction.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to an amino acid-containing gene product.

The term "recombinant protein" refers to a polypeptide of the present invention which is produced by recombinant DNA techniques, wherein generally, DNA encoding an FRP polypeptide is inserted into a suitable expression vector which is in turn used to transform a host cell to produce the heterologous protein. Moreover, the phrase "derived from", with respect to a recombinant FRP gene, is meant to include within the meaning of "recombinant protein" those proteins having an amino acid sequence of a native FRP polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate FRP or Wnt signaling bioactivities.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably an FRP gene.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an FRP polypeptide or, in the case of anti-sense expression from the transferred gene, the expression of a naturally-occurring form of the FRP polypeptide is disrupted.

As used herein, the term "transgene" means a nucleic acid sequence (encoding, e.g., one of the FRP polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

A "Wnt signaling component" refers to a protein or gene encoding a protein involved in a Wnt signaling pathway. Examples of such proteins include: Wnt, frizzled (Fz), disheveled (Dsh), glycogen synthase kinase 3 (GSK3), protein kinase C (APC), β-catenins, and high mobility group (HMG) proteins (e.g. LEF/TCF (Lymphoid Enhancer Factor/T-Cell Factor)).

"Wnt protein" refers to is encoded by a large group of mammalian genes including Wnt3a, Wnt5a, and Wnt5b.

4.3. Prognostics and Diagnostics for Glaucoma

Based on the instant disclosed finding that certain subjects wit glaucoma have increased levels of FRP, a variety of glaucoma diagnostics can be developed. Certain diagnostics can detect mutations in nucleic acid sequences That result in inappropriately high levels of FRP. These diagnostics can be developed based on the known nucleic acid sequence of human FRP cDNA, as shown in FIG. 1 or the encoded amino acid sequence which is shown in FIG. 2. Other diagnostics can be developed based on the genomic sequence of human FRP or of the sequence of genes that regulate FRP expression. Still other diagnostics can be developed based upon a change in the level of FRP gene expression at the mRNA level.

Other diagnostics can detect the activity or level of Wnt signaling proteins or genes encoding Wnt signaling proteins. For example, diagnostics can be developed that detect inappropriately low Wnt signaling activity, including for example, mutations that result in inappropriate functioning of Wnt signaling components, including: frizzled (Fz); disheveled (Dsh); glycogen synthase kinase 3 (GSK3), protein kinase C (APC), β-catenins high mobility group (HMG) proteins (e.g. LEF/TCF (Lymphoid Enhancer Factor/T-Cell Factor)), and hedgehog (Hh). In addition, non-nucleic acid based techniques may be used to detect alteration in the amount or specific activity of any of these Wnt signaling proteins.

A variety of means are currently available for detecting aberrant levels or activities of genes and gene products. For example, many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1: 159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer. J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g., blood, obtained by known techniques (e.g. venipuncture) or saliva. Alternatively, nucleic acid tests can be performed on dry samples (e.g. hair or skin).

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of a Wnt signaling component that is indicative of glaucoma and having about 5, 10, 20, 25, or 30 nucleotides around the mutation or polymorphic region. In a preferred embodiment of the invention, several probes capable of hybridizing specifically to other allelic variants involved in glaucoma are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), and Q-Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of a Wnt signaling component that is indicative of glaucoma under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, aberrant levels or activities of Wnt signaling components that are indicative of glaucoma are identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetraoxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; and Saleeba et al (1992) Methods Enzymol. 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, an appropriate probe is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify aberrant levels or activities of Wnt signaling components that are indicative of glaucoma. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of an allelic variant is carried out using an oligonucleotide ligation assay (OLA), as described, e.g., in U.S. Pat. No. 4,998,617 and in Landegren, U. et al. ((1988) Science 241:1077–1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923–27). In this method, PCR is used to achieve the exponential amplification of target DNA, which is then detected using OLA.

Several techniques based on this OLA method have been developed and can be used to detect aberrant levels or activities of Wnt signaling components that are indicative of glaucoma. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microliter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing glaucoma. This kit may contain one or more oligonucleotides, including 5' and 3' oligonucleotides that hybridize 5' and 3' to at least one Wnt signaling component. PCR amplification oligonucleotides should hybridize between 25 and 2500 base pairs apart, preferably between about 100 and about 500 bases apart, in order to produce a PCR product of convenient size for subsequent analysis.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, and the like; DNA purification reagents such as Nucleon™ kits, lysis buffers, proteinase solutions and the like; PCR reagents, such as 10× reaction buffers, thermostable polymerase, dNTPs, and the like; and allele detection means such as restriction enzyme, allele specific oligonucleotides, degenerate oligonucleotide primers for nested PCR from dried blood.

4.4. Screening Assays for Glaucoma Therapeutics

The invention further provides screening methods for identifying glaucoma therapeutics. A glaucoma therapeutic can be any type of compound, including a protein, a peptide, peptidomimetic, small molecule, and nucleic acid. A nucleic acid can be, e.g., a gene, an antisense nucleic acid, a ribozyme, or a triplex molecule. A glaucoma therapeutic of the invention can be an agonist of a Wnt signaling component activity or an antagonist of FRP or a Wnt signaling antagonistic activity. Preferred agonists include Wnt signaling components or genes and proteins whose expression is regulated by Wnt signaling.

The invention also provides screening methods for identifying glaucoma therapeutics which are capable of binding to an FRP protein, thereby interfering with its blocking of Wnt signaling or therapeutics, which are capable of binding to a Wnt signaling component, thereby agonizing the Wnt signaling component activity.

The compounds of the invention can be identified using various assays depending on the type of compound and activity of the compound that is desired. Set forth below are at least some assays that can be used for identifying glaucoma therapeutics. It is within the skill of the art to design additional assays for identifying glaucoma therapeutics based on the Wnt signaling based activation of trabecular meshwork genes.

4.4.1 Cell-free Assays

Cell-free assays can be used to identify compounds which are capable of interacting with an FRP, Wnt signaling component or a binding partner thereof. Such a compound can, e.g., modify the structure of an FRP, Wnt signaling component or binding partner and thereby effect its activity. Cell-free assays can also be used to identify compounds which modulate the interaction between an FRP or Wnt signaling component and an binding partner. In a preferred embodiment, cell-free assays for identifying such compounds consist essentially in a reaction mixture containing an FRP or Wnt signaling component and a test compound or a library of test compounds in the presence or absence of a binding partner. A test compound can be, e.g., a derivative of a binding partner, e.g., an biologically inactive target peptide, or a small molecule.

Accordingly, one exemplary screening assay of the present invention includes the steps of contacting an FRP, Wnt signaling component or functional fragment thereof or a binding partner with a test compound or library of test compounds and detecting the formation of complexes. For detection purposes, the molecule can be labeled with a specific marker and the test compound or library of test compounds labeled with a different marker. Interaction of a test compound with an FRP, Wnt signaling component or fragment thereof or binding partner thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the FRP, Wnt signaling component, functional fragment thereof, or binding partner thereof is then flown continuously over the sensor surface. A change in the resonance angle as shown on a signal recording, indicates that an interaction has occurred. This technique is further described, e.g., in BIA technology Handbook by Pharmacia.

Another exemplary screening assay of the present invention includes the steps of (a) forming a reaction mixture including: (i) an FRP or Wnt signaling component, (ii) a binding partner thereof; and (iii) a test compound; and (b) detecting interaction of the FRP or Wnt signaling component and the binding protein. The FRP or Wnt signaling component and binding partner can be produced recombinantly, purified from a source, e.g., plasma, or chemically synthesized, as described herein. A statistically significant change (potentiation or inhibition) in the interaction of the FRP or Wnt signaling component and the binding protein in the presence of the test compound, relative to the interaction in the absence of the test compound, indicates a potential agonist (mimetic or potentiator) or antagonist (inhibitor) of FRP or Wnt signaling bioactivity for the test compound. The compounds of this assay can be contacted simultaneously. Alternatively, an FRP or Wnt signaling component can first be contacted with a test compound for an appropriate amount of time, following which the binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified FRP or Wnt signaling components are added to a composition containing the FRP binding partner or Wnt signaling component binding partner, and the formation of a complex is quantitated in the absence of the test compound.

Complex formation between an FRP protein and an FRP binding partner may be detected by a variety of techniques. Modulation of the formation of complexes can be quantitated using, for example, detectably labeled proteins such as radiolabeled, fluorescently labeled, or enzymatically labeled FRP, Wnt signaling component or binding partners, by immunoassay, or by chromatographic detection.

Typically, it will be desirable to immobilize FRP, a Wnt signaling component or its binding partner to facilitate separation of complexes from uncomplexed forms of one or both of the proteins, as well as to accommodate automation of the assay. Binding of FRP or a Wnt signaling component to a binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the binding partner, e.g. a 35S-labeled binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of the FRP or Wnt signaling component or binding partner found in the bead fraction quantitated from the gel using standard electrophoretic techniques such as described in the appended examples.

Other techniques for immobilizing proteins on matrices are also available for use in the subject assay. For instance, FRP, a Wnt signaling component or its cognate binding partner can be immobilized utilizing conjugation of biotin and streptavidin. For instance, biotinylated FRP or Wnt signaling components can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with FRP or a Wnt signaling component can be derivatized to the wells of the plate, and FRP or Wnt signaling components trapped in the wells by antibody conjugation. As above, preparations of an FRP or Wnt signaling component, a binding protein and a test compound are incubated in the FRP or Wnt signaling component presenting wells of the plate, and the amount of complex trapped in the well can be quantitated. Exemplary methods for detecting such complexes, in addition to those described above for the GST-immobilized complexes, include immunodetection of complexes using antibodies reactive with the FRP or Wnt signaling component binding partner, or which are reactive with FRP or a Wnt signaling component protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the binding partner. To illustrate, the binding partner can be chemically cross-linked or genetically fused with horseradish peroxidase, and the amount of polypeptide trapped in the complex can be assessed with a chromogenic substrate of the enzyme, e.g. 3,3'-diaminobenzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein can be used. Alternatively, the protein to be detected in the complex can be "epitope tagged" in the form of a fusion protein which includes, in addition to the FRP or Wnt signaling component sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, N.J.).

Cell-free assays can also be used to identify compounds which interact with an FRP or Wnt signaling component and modulate their activity. Accordingly, in one embodiment, an FRP or Wnt signaling component is contacted with a test compound and the catalytic activity of FRP or the Wnt signaling component is monitored. In one embodiment, the ability of FRP or a Wnt signaling component to bind to a target peptide is determined according to methods known in the art.

4.4.2. Cell Based Assays

In addition to cell-free assays, such as described above, FRP proteins as provided by the present invention, facilitate the generation of cell-based assays, e.g., for identifying small molecule agonists or antagonists. In one embodiment, a cell expressing an FRP protein on the outer surface of its cellular membrane is incubated in the presence of a test compound alone or a test compound and a molecule which is known to interact with FRP and the interaction between FRP and a test compound is detected, e.g., by using a microphysiometer (McConnell et al. (1992) Science 257: 1906). An interaction between the FRP protein the test compound is detected by the microphysiometer as a change in the acidification of the medium. In preferred embodiments, the cell based assays of the invention utilize human cells obtained from the trabecular meshwork ocular tissue of normal or glaucoma-affected patients.

The propagation of human trabecular cells in culture allows the study of the structural and functional properties of this distinct cell type under reproducible experimental conditions. Human trabecular cells can be effectively grown from dissected explants of trabecular tissue, and the cultured cells can maintain the distinctive ultrastructural features of uncultured trabecular cells through numerous passages in vitro. The trabecular cell possesses a wide range of biochemical and structural properties that may be important for the maintenance of the aqueous outflowpathway. These properties include the growth of trabecular cells as an endothelial monolayer with a nonthrombogenic cell surface, the production of plasminogen activator, avid phagocytosis, and the ability to synthesize glycosaminoglycans, collagen, fibronectin, and other connective tissue elements. The presence of hyaluronidase and other lysosomal enzymes emphasizes that human trabecular cells are capable of metabolizing hyaluronic acid and other extracellular materials. Potential mechanisms of trabecular cell damage in vitro may be examined by evaluating, for example, the effects of extended passage, peroxide exposure, and laser treatment on cellular morphology.

Cell based assays based upon trabecular meshwork cells or other cell types can also be used to identify compounds which modulate expression of an FRP gene, modulate translation of an FRP mRNA, or which modulate the stability of an FRP mRNA or protein. Accordingly, in one embodiment, a cell which is capable of producing FRP, e.g., a trabecular meshwork cell, is incubated with a test compound and the amount of FRP produced in the cell medium is measured and compared to that produced from a cell which has not been contacted with the test compound. The specificity of the compound vis a vis FRP can be confirmed by various control analysis, e.g., measuring the expression of one or more control genes.

Compounds which can be tested include small molecules, proteins, and nucleic acids. In particular, this assay can be used to determine the efficacity of FRP antisense molecules or ribozymes.

In another embodiment, the effect of a test compound on transcription of an FRP gene is determined by transfection experiments using a reporter gene operatively linked to at least a portion of the promoter of an FRP gene. A promoter region of a gene can be isolated, e.g., from a genomic library according to methods known in the art. The reporter gene can be any gene encoding a protein which is readily quantifiable, e.g., the luciferase or CAT gene, well known in the art.

In a preferred embodiment, the reporter gene is a natural or synthetic gene which is transcriptionally activated in response to a Wnt signal. For example, the engrailed gene is activated in response to Wnt induction. Furthermore, increased expression of engrailed results in the transcriptional induction of the hedgehog gene, which is therefor now activated in response to Wnt. Finally, synthetic reporter genes which are activated by nuclear LEF(tcf)/beta-catenin also provide sensitive reporter genes for measuring Wnt induction.

This invention further pertains to novel agents identified by the above-described screening assays and uses thereof for treatments as described herein.

4.5. Methods of Treating Disease

A "glaucoma therapeutic," whether an antagonist or agonist can be, as appropriate, any of the preparations described above, including isolated polypeptides, gene therapy constructs, antisense molecules, peptidomimetics, small molecules, non-nucleic acid, non-peptidic or agents identified in the drug assays provided herein.

The present invention provides for both prophylactic and therapeutic methods of treating a subject having or likely to develop a disorder associated with aberrant FRP or Wnt pathway component genes expression or activity, e.g., glaucoma.

4.5.1. Prophylactic Methods

In one aspect, the invention provides a method for preventing in a subject, a disease or condition associated with an aberrant FRP or Wnt pathway component genes expression or activity by administering to the subject an agent which modulates FRP or Wnt pathway component genes expression or at least one FRP or Wnt pathway component genes activity. Subjects at risk for such a disease can be identified by a diagnostic or prognostic assay, e.g., as described herein. Administration of a prophylactic agent can occur prior to the manifestation of symptoms characteristic of the FRP or Wnt pathway component genes aberrancy, such that a disease or disorder is prevented or, alternatively, delayed in its progression. Depending on the type of FRP or Wnt pathway component genes aberrancy, for example, a FRP or Wnt pathway component genes agonist or FRP or Wnt pathway component genes antagonist agent can be used for treating the subject prophylactically. The prophylactic methods are similar to therapeutic methods of the present invention and are further discussed in the following subsections.

4.5.2. Therapeutic Methods

In general, the invention provides methods for treating a disease or condition which is caused by or contributed to by an aberrant FRP or Wnt pathway component genes activity comprising administering to the subject an effective amount of a compound which is capable of modulating an FRP or Wnt pathway component genes activity. Among the approaches which may be used to ameliorate disease symptoms involving an aberrant FRP or Wnt pathway component genes activity are, for example, antisense, ribozyme, and triple helix molecules or small organic agents as described above. Examples of suitable compounds include the antagonists, agonists or homologues described in detail herein.

4.5.3. Effective Dose

Toxicity and therapeutic efficacy of such compounds can be determined by standard pharmaceutical procedures in cell cultures or experimental animals, e.g., for determining The $LD_{50}$ (The Dose Lethal To 50% Of The Population) And The $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include concentrations $\chi$ the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ to include concentrations $\chi$ the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.4. Monitoring of Effects of FRP/Wnt Therapeutics During Clinical Trials The ability to target populations expected to show the highest clinical benefit, based on the FRP or Wnt pathway component genes or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of FRP or Wnt pathway component genes as a marker is useful for optimizing effective dose).

The treatment of an individual with an FRP or Wnt pathway component genes therapeutic can be monitored by determining FRP or Wnt pathway component genes characteristics, such as FRP or Wnt pathway component genes protein level or activity, FRP or Wnt pathway component genes mRNA level, and/or FRP or Wnt pathway component genes transcriptional level. This measurements will indicate whether the treatment is effective or whether it should be adjusted or optimized. Thus, FRP or Wnt pathway component genes can be used as a marker for the efficacy of a drug during clinical trials.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a preadministration sample from a subject prior to administration of the agent; (ii) detecting the level of expression of an FRP or Wnt pathway component genes protein, mRNA, or genomic DNA in the preadministration sample; (iii) obtaining one or more post-administration samples from the subject; (iv) detecting the level of expression or activity of the FRP or Wnt pathway component genes protein, mRNA, or genomic DNA in the post-administration samples; (v) comparing the level of expression or activity of the FRP or Wnt pathway component genes protein, mRNA, or genomic DNA in the preadministration sample with the FRP or Wnt pathway component genes protein, mRNA, or genomic DNA in the post administration sample or samples; and (vi) altering the administration of the agent to the subject accordingly. For example, increased administration of the agent may be desirable to increase the expression or activity of FRP or Wnt pathway component genes to higher levels than detected, i.e., to increase the effectiveness of the agent. Alternatively, decreased administration of the agent may be desirable to decrease expression or activity of FRP or Wnt pathway component genes to lower levels than detected, i.e., to decrease the effectiveness of the agent.

Cells of a subject may also be obtained before and after administration of an FRP or Wnt pathway component genes therapeutic to detect the level of expression of genes other than FRP or Wnt pathway component genes, to verify that the FRP or Wnt pathway component genes therapeutic does not increase or decrease the expression of genes which could be deleterious. This can be done, e.g., by using the method of transcriptional profiling. Thus, mRNA from cells exposed in vivo to an FRP or Wnt pathway component genes therapeutic and mRNA from the same type of cells that were not exposed to the FRP or Wnt pathway component genes therapeutic could be reverse transcribed and hybridized to a chip containing DNA from numerous genes, to thereby compare the expression of genes in cells treated and not treated with an FRP or Wnt pathway component genes-therapeutic. If, for example an FRP or Wnt pathway component genes therapeutic turns on the expression of a proto-oncogene in an individual, use of this particular FRP or Wnt pathway component genes therapeutic may be undesirable.

4.5.5. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or topical, oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. Injection is not likely to be the preferred method of systemic administration; oral dosage forms are. Topical ophthalmic compositions the compounds of the invention can be formulate with one or more pharmceutically acceptable excipients, such as buffering agents, preservatives (including preservative adjuncts), tonicity-adjusting agents, surfactants, solubilizing agents stabilizing agents, comfort-enhancing agents, emollients, pH-adjusting agents and lubricants. Topically administrable ophthalmic compositions will generally be formulated at pH 4.5–8 and have an osmolarity of 26–320 mOSm/kg. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ation oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered topically, by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic FRP or Wnt pathway component gene can be introduced into a patient by any of a number of methods, each of which is familiar in the art. For instance, a pharmaceutical preparation of the gene delivery system can be introduced by intraocular injection or systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). An FRP or Wnt pathway component genes gene can be delivered in a gene therapy construct by electroporation using techniques described, for example, by Dev et al. ((1994) Cancer Treat Rev 20:105–115) or by transcleral iontophoresis.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.6. Kits

The invention further provides kits for use in diagnostics or prognostic methods or for treating a disease or condition associated with an aberrant FRP or Wnt pathway component genes protein. The invention also provides kits for determining which FRP or Wnt pathway component genes therapeutic should be administered to a subject. The invention encompasses kits for detecting the presence of FRP or Wnt pathway component genes mRNA or protein in a biological sample or for determining the presence of mutations or the identity of polymorphic regions in an FRP or Wnt pathway component genes gene. For example, the kit can comprise a labeled compound or agent capable of detecting FRP or Wnt pathway component genes protein or mRNA in a biological sample; means for determining the amount of FRP or Wnt pathway component genes in the sample; and means for comparing the amount of FRP or Wnt pathway component genes in the sample with a standard. The compound or agent can be packaged in a suitable container. The kit can further comprise instructions for using the kit to detect FRP or Wnt pathway component genes mRNA or protein.

In one embodiment, the kit comprises a pharmaceutical composition containing an effective amount of an FRP or Wnt pathway component genes antagonist therapeutic and instruction for use in treating or preventing hypertension. In another embodiment, the kit comprises a pharmaceutical composition comprising an effective amount of an FRP or Wnt pathway component genes agonist therapeutic and instructions for use in treating eye disorders or diseases such as glaucoma. Generally, the kit comprises a pharmaceutical composition comprising an effective amount of an FRP or Wnt pathway component genes agonist or antagonist therapeutic and instructions for use as a glaucoma therapeutic agent. For example, the kit can comprise a pharmaceutical composition comprising an effective amount of an FRP or Wnt pathway component genes agonist therapeutic and instructions for use as an analgesic.

Yet other kits can be used to determine whether a subject has or is likely to develop a disease or condition associated with an aberrant FRP or Wnt pathway component genes activity. Such a kit can comprise, e.g., one or more nucleic acid probes capable of hybridizing specifically to at least a portion of an FRP or Wnt pathway component genes gene or allelic variant thereof, or mutated form thereof.

4.7. Additional Uses for FRP or Wnt Pathway Gene Proteins and Nucleic Acids

The FRP or Wnt pathway component genes nucleic acids of the invention can further be used in the following assays. In one embodiment, the human FRP or Wnt pathway component genes nucleic acid having SEQ ID NO:1 or a portion thereof, or a nucleic acid which hybridizes thereto can be used to determine the chromosomal localization of an FRP or Wnt pathway component genes gene. Comparison of the chromosomal location of the FRP or Wnt pathway component genes gene with the location of chromosomal regions which have been shown to be associated with specific diseases or conditions, e.g., by linkage analysis (coinheritance of physically adjacent genes), can be indicative of diseases or conditions in which FRP or Wnt pathway component genes may play a role. A list of chromosomal regions which have been linked to specific diseases can be found, for example, in V. McKusick, Mendelian Inheritance in Man (available on line through Johns Hopkins University Welch Medical Library) and through the National Center for Biotechnology Information, National Library of Medicine, National Institutes of Health, Bethesda, Md. (Online Mendelian Inheritance in Man)). Furthermore, the FRP or Wnt pathway component genes gene can also be used as a chromosomal marker in genetic linkage studies involving genes other than FRP or Wnt pathway component genes.

Chromosomal localization of a gene can be performed by several methods well known in the art. For example, Southern blot hybridization or PCR mapping of somatic cell hybrids can be used for determining on which chromosome or chromosome fragment a specific gene is located. Other mapping strategies that can similarly be used to localize a gene to a chromosome or chromosomal region include in situ hybridization, prescreening with labeled flow-sorted chromosomes and preselection by hybridization to construct chromosome specific-cDNA libraries.

Furthermore, fluorescence in situ hybridization (FISH) of a nucleic acid, e.g., an FRP or Wnt pathway component genes nucleic acid, to a metaphase chromosomal spread is a one step method that provides a precise chromosomal location of the nucleic acid. This technique can be used with nucleic acids as short as 500 or 600 bases; however, clones larger than 2,000 bp have a higher likelihood of binding to a unique chromosomal location with sufficient signal intensity for simple detection. Such techniques are described, e.g., in Verma et al., Human Chromosomes: a Manual of Basic Techniques, Pergamon Press, New York (1988). Using such techniques, a gene can be localized to a chromosomal region containing from about 50 to about 500 genes.

If the FRP or Wnt pathway component genes gene is shown to be localized in a chromosomal region which cosegregates, i.e., which is associated, with a specific disease, the differences in the cDNA or genomic sequence between affected and unaffected individuals are determined. The presence of a mutation in some or all of the affected individuals but not in any normal individuals, will be indicative that the mutation is likely to be causing or contributing to the disease.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization(B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

4.8. Pharmacogenomics

Knowledge of the particular alteration or alterations, resulting in defective or deficient FRP or Wnt pathway component genes or proteins in an individual (the FRP or Wnt pathway component genes genetic profile), alone or in conjunction with information on other genetic defects contributing to the same disease (the genetic profile of the particular disease) allows a customization of the therapy for a particular disease to the individual's genetic profile, the goal of "pharmacogenomics". For example, subjects having a specific allele of an FRP or Wnt pathway component genes gene may or may not exhibit symptoms of a particular disease or be predisposed of developing symptoms of a particular disease. Further, if those subjects are symptomatic, they may or may not respond to a certain drug, e.g., a specific FRP or Wnt pathway component genes therapeutic, but may respond to another. Thus, generation of an FRP or Wnt pathway component genes genetic profile, (e.g., categorization of alterations in FRP or Wnt pathway component genes gene which are associated with the development of a particular disease), from a population of subjects, who are symptomatic for a disease or condition that is caused by or contributed to by a defective and/or deficient FRP or Wnt pathway component genes gene and/or protein (an FRP or Wnt pathway component genes genetic population profile) and comparison of an individual's FRP or Wnt pathway component genes profile to the population profile, permits the selection or design of drugs that are expected to be safe and efficacious for a particular patient or patient population (i.e., a group of patients having the same genetic alteration).

For example, an FRP or Wnt pathway component genes population profile can be performed, by determining the FRP or Wnt pathway component genes profile, e.g., the identity of FRP or Wnt pathway component genes genes, in a patient population having a disease, which is caused by or contributed to by a defective or deficient FRP or Wnt pathway component genes gene. Optionally, the FRP or Wnt pathway component genes population profile can further include information relating to the response of the population to an FRP or Wnt pathway component genes therapeutic, using any of a variety of methods, including, monitoring: 1) the severity of symptoms associated with the FRP or Wnt pathway component genes related disease, 2) FRP or Wnt pathway component genes gene expression level, 3) FRP or Wnt pathway component genes mRNA level, and/or 4) FRP or Wnt pathway component genes protein level. and (iii) dividing or categorizing the population based on the particular genetic alteration or alterations present in its FRP or Wnt pathway component genes gene or an FRP or Wnt pathway component genes pathway gene. The FRP or Wnt pathway component genes genetic population profile can also, optionally, indicate those particular alterations in which the patient was either responsive or non-responsive to a particular therapeutic. This information or population profile, is then useful for predicting which individuals should respond to particular drugs, based on their individual FRP or Wnt pathway component genes profile.

In a preferred embodiment, the FRP or Wnt pathway component genes profile is a transcriptional or expression level profile and step (i) is comprised of determining the expression level of FRP or Wnt pathway component genes proteins, alone or in conjunction with the expression level of other genes, known to contribute to the same disease. The FRP or Wnt pathway component genes profile can be measured in many patients at various stages of the disease.

Pharmacogenomic studies can also be performed using transgenic animals. For example, one can produce transgenic mice, e.g., as described herein, which contain a specific allelic variant of an FRP or Wnt pathway component genes gene. These mice can be created, e.g., by replacing their wild-type FRP or Wnt pathway component genes gene with an allele of the human FRP or Wnt pathway component genes gene. The response of these mice to specific FRP or Wnt pathway component genes therapeutics can then be determined.

4.9. Transgenic Animals

The invention further provides for transgenic animals, which can be used for a variety of purposes, e.g., to identify glaucoma therapeutics. Transgenic animals of the invention include non-human animals containing mutations in nucleic acid sequences that result in inappropriately high levels of FRP (e.g. mutations in genes encoding transcription factors that regulate expression of FRP). Alternatively, transgenic animals can contain mutations in Wnt signaling components, including: frizzled (Fz); disheveled (Dsh); glycogen synthase kinase 3 (GSK3), protein kinase C (APC), β-catenins and high mobility group (HMG) proteins (e.g. LEF/TCF (Lymphoid Enhancer Factor/T-Cell Factor)). Such animals can be used, e.g., to determine the effect on phenotype of interfering with the expression in trabecular meshwork cells of genes whose expression is regulated by Wnt signaling.

The transgenic animals can also be animals containing a transgene, such as reporter gene, under the control of an FRP promoter or fragment thereof. These animals are useful, e.g., for identifying drugs that modulate production of FRP, such as by modulating FRP gene expression. An FRP gene promoter can be isolated, e.g., by screening of a genomic library with an FRP cDNA fragment and characterized according to methods known in the art.

Yet other non-human animals within the scope of the invention include genes encoding Wnt signaling components in which the expression of the endogenous gene has been mutated or "knocked out". These animals could be useful to determine whether the absence of a Wnt signaling component will result in a specific phenotype. Methods for obtaining transgenic and knockout non-human animals are well known in the art and are discussed herein.

In a preferred embodiment, the invention provides transgenic non-human animals for use in the development of glaucoma diagnostic and therapeutic methods. For example, in certain preferred embodiments, the transgenic animals of the invention comprise an heterologous FRP expressing gene which results in an increase in the level of FRP gene expression in an ocular tissue. In preferred embodiments, the ocular tissue is the trabecular meshwork and the FRP-overexpressing cells are trabecular meshwork cells. In still more preferred embodiments the transgenic non-human animals expressing increased levels of FRP in the trabecular meshwork cells have at least one symptom characteristic of glaucoma, such as an increased intraocular pressure (IOP). In certain preferred embodiments, the transgenic animals of the invention provide an in vivo assay system for the screening of glaucoma therapeutics compounds and the development of glaucoma diagnostics.

4.9.1 Animal-based Systems

Another aspect of the present invention concerns transgenic animals which are comprised of cells (of that animal) which contain a transgene of the present invention and which preferably (though optionally) express an exogenous FRP protein in one or more cells in the animal. A FRP transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a FRP protein can be essential for many forms of lineage analysis and can additionally provide a means to assess the effects of, for example, lack of FRP expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject FRP proteins. For example, excision of a target sequence which interferes with the expression of a recombinant FRP gene, such as one which encodes an antagonistic homolog or an antisense transcript, can be designed to activate expression of that gene. This interference with expression of the protein can result from a variety of mechanisms, such as spatial separation of the FRP gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell function, cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251: 1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant FRP protein can be regulated via control of recombinase expression.

Use of the cre/loxP recombinase system to regulate expression of a recombinant FRP protein requires the construction of a transgenic animal containing transgenes encoding both the Cre recombinase and the subject protein. Animals containing both the Cre recombinase and a recombinant FRP gene can be provided through the construction of "double" transgenic animals. A convenient method for providing such animals is to mate two transgenic animals each containing a transgene, e.g., a FRP gene and recombinase gene.

One advantage derived from initially constructing transgenic animals containing a FRP transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic FRP transgene is silent will allow the study of progeny from that founder in which disruption of FRP mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the FRP transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a FRP A transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-2b, H-2d or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by PCR, Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a FRP protein (either agonistic or antagonistic), and antisense transcript, or a FRP mutant. Further, in such embodiments the sequence may be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154–156; Bradley et al. (1984) Nature 309:255–258; Gossler et al. (1986) PNAS 83: 9065–9069; and Robertson et al. (1986) Nature 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468–1474.

In one embodiment, gene targeting, which is a method of using homologous recombination to modify an animal's genome, can be used to introduce changes into cultured embryonic stem cells. By targeting a FRP gene of interest in ES cells, these changes can be introduced into the germlines of animals to generate chimeras. The gene targeting procedure is accomplished by introducing into tissue culture cells a DNA targeting construct that includes a segment homologous to a target FRP locus, and which also includes an intended sequence modification to the FRP genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a FRP gene function through the use of a targeting transgene construct designed to undergo homologous recombination with one or more FRP genomic sequences. The targeting construct can be arranged so that, upon recombination with an element of a FRP gene, a positive selection marker is inserted into (or replaces) coding sequences of the gene. The inserted sequence functionally disrupts the FRP gene, while also providing a positive selection trait. Exemplary FRP targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp. Morphol.* 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence Alternatively, PCR can be used. Finally, if the marker gene is a gene that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the FRP coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, as the appended Examples describe, the transformed ES cells can be microinjected into blastocytes.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knock-out offspring are available. For example, Northern blots can be used to probe the mRNA for the presence or absence of transcripts encoding either the gene knocked out, the marker gene, or both. In addition, Western blots can be used to assess the level of expression of the FRP gene knocked out in various tissues of the offspring by probing the Western blot with an antibody against the particular FRP protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a FRP-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), Immunochemical *Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The present invention is further illustrated by the following examples which should not be construed as limiting in any way. The contents of all cited references (including literature references, issued patents, published patent applications, and co-pending patent applications) cited throughout this application are hereby expressly incorporated by reference.

5.1 Association of Frizzle Related Protein 1 (FRP-1) and Glaucoma

Materials and Methods

Frizzled Related Protein cDNA Sequence Identified by RNA Differential Display

AACAGCCTGCCTGTCCCCCCGCACTTTTTACATATATTTGTTTCATTTCTGCAGATGGAAAG

TTGACATGGGTGGGTGTCCCCATCCAGCGAGAGAGTTTCAAAAGCAAAACATCTCTGCAGTTTTTC

CCAAGTACCCTGAGATACTTCCCAAAGCCCTTATGTTTAATCAGCGATGTATATAAGCCAGTTCACT

TAGACAACTTTACCCTTCTTGTCCAATGTACAGGAAGTAGTTCT (SEQ ID NO: 3).

5.2. Expression of Recombinant FRP or Wnt Pathway Genes in COS Cells

This example describes a method for producing recombinant full length human FRP or Wnt pathway component genes in a mammalian expression system.

An expression construct containing a nucleic acid encoding a full length human FRP or Wnt pathway component genes protein, or a soluble FRP or Wnt pathway component genes protein can be constructed as follows. A nucleic acid encoding the full length human FRP or Wnt pathway component genes protein or a soluble form of FRP or Wnt pathway component genes protein described above is obtained by reverse transcription (RT-PCR) of mRNA extracted from human cells expressing FRP or Wnt pathway component genes, e.g., human trabecullar meshwork cells using PCR primers based on the sequence set forth in SEQ ID NO: 1. The PCR primers further contain appropriate restriction sites for introduction into the expression plasmid. The amplified nucleic acid is then inserted in a eukaryotic expression plasmid such as pcDNAI/Amp (In Vitrogen) containing: 1) SV40 origin of replication, 2) ampicillin resistance gens, 3) *E. coli* replication origin, 4) CMV promoter followed by a polylinker region, a SV40 intron and polyadenylation site. A DNA fragment encoding the full length human FRP or Wnt pathway component genes and a HA or myc tag fused in frame to its 3' end is then cloned into the polylinker region of the. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to FRP or Wnt pathway component genes allows easy detection of the recombinant protein with an antibody that recognizes the HA epitope.

For expression of the recombinant FRP or Wnt pathway component genes, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the FRP or Wnt pathway component genes-HA protein can be detected by radiolabelling and immunoprecipitation with an anti-HA antibody. (E. Harlow, D. Lane, Antibodies: A Laboratory Manual, Cold Spring Harbor Laboratory Press, (1988)). For this, transfected cells are labeled with $^{35}$S-cysteine two days post transfection. The cells, or alternatively the culture media (e.g., for the soluble FRP or Wnt pathway component genes) is then collected and the FRP or Wnt pathway component genes protein immunoprecipitated with an HA specific monoclonal antibody. Alternatively, expression of the recombinant protein can be detected by Western blot analysis. To determine whether full length FRP or Wnt pathway component genes is a membrane protein, and/or a secreted protein, the cells transfected with a vector encoding the fall length FRP or Wnt pathway component genes protein can be lysed with detergent (RIPA buffer (150 mM NaCl 1% NP-40, 0.1% SDS, 1% NP-40, 0.5% DOC, 50 mM Tris, pH 7.5). (Wilson, I. et al., Id. 37:767 (1984)). Proteins precipitated can then be analyzed on SDS-PAGE gel. Thus, the presence of FRP or Wnt pathway component genes in the cell will be indicative that the full length FRP or Wnt pathway component genes can be membrane bound and the presence of FRP or Wnt pathway component genes in the supernatant will be indicative that the protein can also be in a soluble form, whether produced as a secreted protein or released by leakage from the cell.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A method for diagnosing glaucoma comprising detecting the expression level of mRNA encoding human frizzled related protein-1 (FRP-1), the amino acid sequence of which is set forth in SEQ ID NO:2, in a patient sample of trabecular meshwork (TM) cells, wherein the detecting comprises utilizing a hybridization assay using a nucleic acid probe that specifically hybridizes to the mRNA encoding FRP-1, wherein an aberrantly high level of the mRNA relative to that of a normal person is diagnostic of a glaucomatous state.

2. The method of claim 1, wherein the expression level of the mRNA encoding FRP-1 is determined by detecting the formation of a complex of the mRNA and the nucleic acid probe that specifically hybridizes to the mRNA.

3. The method of claim 2, wherein the nucleic acid probe is fluorescently labeled.

* * * * *

SEQUENCE LISTING

```
<160> NUMBER OF SEQ ID NOS: 3

<210> SEQ ID NO 1
<211> LENGTH: 4469
<212> TYPE: DNA
<213> ORGANISM: Homo sapiens

<400> SEQUENCE: 1
cctgcagcct ccggagtcag tgccgcgcgc ccgccgcccc gcgccttcct gctcgccgca      60
cctccgggag ccggggcgca cccagcccgc agcgccgcct ccccgcccgc gccgcctccg     120
accgcaggcc gagggccgcc actggccggg gggaccgggc agcagcttgc ggccgcggag     180
ccgggcaacg ctggggactg cgccttttgt ccccggaggt ccctggaagt ttgcggcagg     240
acgcgcgcgg ggaggcggcg gaggcagccc cgacgtcgcg gagaacaggg cgcagagccg     300
gcatgggcat cgggcgcagc gaggggggcc gccgcgggc cctgggcgtg ctgctggcgc      360
tgggcgcggc gcttctggcc gtgggctcgg ccagcgagta cgactacgtg agcttccagt     420
cggacatcgg cccgtaccag agcgggcgct tctacaccaa gccacctcag tgcgtggaca     480
tccccgcgga cctgcggctg tgccacaacg tgggctacaa gaagatggtg ctgcccaacc     540
tgctggagca cgagaccatg gcggaggtga agcagcaggc cagcagctgg gtgcccctgc     600
tcaacaagaa ctgccacgcc gggacccagg tcttcctctg ctcgctcttc gcgcccgtct     660
gcctggaccg gcccatctac ccgtgtcgct ggctctgcga ggccgtgcgc gactcgtgcg     720
agccggtcat gcagttcttc ggcttctact ggcccgagat gcttaagtgt gacaagttcc     780
cggaggggga cgtctgcatc gccatgacgc cgcccaatgc caccgaagcc tccaagcccc     840
aaggcacaac ggtgtgtcct ccctgtgaca acgagttgaa atctgaggcc atcattgaac     900
atctctgtgc cagcgagttt gcactgagga tgaaaataaa agaagtgaaa aagaaaatg      960 gcgacaagaa gattgtcccc aagaagaaga agcccctgaa gttggggccc atcaagaaga    1020
aggacctgaa gaagcttgtg ctgtacctga agaatgggc tgactgtccc tgccaccagc     1080
tggacaacct cagccaccac ttcctcatca tgggccgcaa ggtgaagagc cagtacttgc     1140
tgacggccat ccacaagtgg gacaagaaaa acaaggagtt caaaaacttc atgaagaaaa    1200
tgaaaaacca tgagtgcccc acctttcagt ccgtgtttaa gtgattctcc cggggggcagg    1260
```

-continued

```
gtggggaggg agcctcgggt ggggtgggag cggggggggac agtgcccggg aacccgtggt    1320
cacacacacg cactgccctg tcagtagtgg acattgtaat ccagtcggct tgttcttgca    1380
gcattcccgc tccctttccc tccatagcca cgctccaaac cccagggtag ccatggccgg    1440
gtaaagcaag ggccatttag attaggaagg tttttaagat ccgcaatgtg gagcagcagc    1500
cactgcacag gaggaggtga caaaccattt ccaacagcaa cacagccact aaaacacaaa    1560
aaggggatt gggcggaaag tgagagccag cagcaaaaac tacattttgc aacttgttgg    1620
tgtggatcta ttggctgatc tatgcctttc aactagaaaa ttctaatgat tggcaagtca    1680
cgttgttttc aggtccagag tagtttcttt ctgtctgctt taaatggaaa cagactcata    1740
ccacacttac aattaaggtc aagcccagaa agtgataagt gcagggagga aaagtgcaag    1800
tccattatct aatagtgaca gcaaagggac caggggagag gcattgcctt ctctgcccac    1860
agtcttccg tgtgattgtc tttgaatctg aatcagccag tctcagatgc cccaaagttt    1920
cggttcctat gagcccgggg catgatctga tccccaagac atgtggaggg gcagcctgtg    1980
cctgcctttg tgtcagaaaa aggaaaccac agtgagcctg agagacgg cgattttcgg     2040
gctgagaagg cagtagtttt caaaacacat agttaaaaaa gaaacaaatg aaaaaaattt    2100
tagaacagtc cagcaaattg ctagtcaggg tgaattgtga aattgggtga agagcttagg    2160
attctaatct catgttttt ccttttcaca tttttaaaag aacaatgaca aacacccact    2220
tattttcaa ggttttaaaa cagtctatact tgagcatttg aaaggtgtgc tagaacaagg    2280
tctcctgatc cgtccgaggc tgcttcccag aggagcagct ctccccaggc atttgccaag    2340
ggaggcggat ttccctggta gtgtagctgt gtggcttttcc ttcctgaaga gtccgtggtt    2400
gccctagaac ctaacacccc ctagcaaaac tcacagagct ttccgttttt ttcttcctg    2460
taaagaaaca tttcctttga acttgattgc ctatggatca agaaattca gaacagcctg    2520
cctgttcccc cgcactttt acatatattt gtttcatttc tgcagatgga aagttgacat    2580
gggtggggtg tccccatcca gcgagagagt ttcaaaagca aaacatctct gcagtttttc    2640
ccaagtaccc tgagatactt cccaaagccc ttatgtttaa tcagcgatgt atataagcca    2700
gttcacttag acaactttac ccttcttgtc caatgtacag gaagtagttc taaaaaaaat    2760
gcatattaat ttcttccccc aaagccggat tcttaattct ctgcaacact ttgaggacat    2820
ttatgattgt ccctctgggc caatgcttat acccagtgag gatgctgcag tgaggctgta    2880
aagtggcccc ctgcggccct agcctgaccc ggagaaagga tggtagattc tgttaactct    2940
tgaagactcc agtatgaaaa tcagcatgcc cgcctagtta cctaccggag agttatcctg    3000
ataaattaac ctctcacagt tagtgatcct gtccttttaa cacctttttt gtggggttct    3060
ctctgacctt tcatcgtaaa gtgctgggga ccttaagtga tttgcctgta attttggatg    3120
attaaaaaat gtgtatatat attagctaat tagaaatatt ctacttctct gttgtcaaac    3180
tgaaattcag agcaagttcc tgagtgcgtg gatctgggtc ttagttctgg ttgattcact    3240
caagagttca gtgctcatac gtatctgctc attttgacaa agtgcctcat gcaaccgggc    3300
cctctctctg cggcagagtc cttagtggag gggtttacct ggaacataag tagttaccac    3360
agaatacgga agagcaggtg actgtgctgt gcagctctct aaatgggaat tctcaggtag    3420
gaagcaacag cttcagaaag agctcaaaat aaattggaaa tgtgaatcgc agctgtgggt    3480
tttaccaccg tctgtctcag agtcccagga ccttgagtgt cattagttac tttattgaag    3540
gttttagacc catagcagct ttgtctctgt cacatcagca atttcagaac caaagggag    3600
```

```
gctctctgta ggcacagagc tgcactatca cgagcctttg ttttctcca caaagtatct    3660 aacaaaacca atgtgcagac tgattggcct ggtcattggt ctccgagaga ggaggtttgc    3720
ctgtgatttg cctgtgattt cctaattatc gctagggcca aggtgggatt tgtaaagctt    3780
tacaataatc attctggata gagtcctggg aggtccttgg cagaactcag ttaaatcttt    3840
gaagaatatt tgtagttatc ttagaagata gcatgggagg tgaggattcc aaaaacattt    3900
tatttttaaa atatcctgtg taacacttgg ctcttggtac ctgtgggtta gcatcaagtt    3960
ctccccaggg tagaattcaa tcagagctcc agtttgcatt tggatgtgta aattacagta    4020
atcccatttc ccaaacctaa aatctgtttt tctcatcaga ctctgagtaa ctggttgctg    4080
tgtcataact tcatagatgc aggaggctca ggtgatctgt ttgaggagag caccctaggc    4140
agcctgcagg gaataacata ctggccgttc tgacctgttg ccagcagata cacaggacat    4200
ggatgaaatt cccgtttcct ctagtttctt cctgtagtac tcctctttta gatcctaagt    4260
ctcttacaaa agctttgaat actgtgaaaa tgttttacat tccatttcat ttgtgttgtt    4320
tttttaactg cattttacca gatgttttga tgttatcgct tatgttaata gtaattcccg    4380
tacgtgttca ttttattttc atgcttttc agccatgtat caatattcac ttgactaaaa    4440
tcactcaatt aatcaatgaa aaaaaaaaa                                      4469

<210> SEQ ID NO 2
<211> LENGTH: 313
<212> TYPE: PRT
<213> ORGANISM: Homo sapiens

<400> SEQUENCE: 2

Met Gly Ile Gly Arg Ser Glu Gly Gly Arg Gly Ala Leu Gly Val
 1               5                  10                  15

Leu Leu Ala Leu Gly Ala Ala Leu Leu Ala Val Gly Ser Ala Ser Glu
                20                  25                  30

Tyr Asp Tyr Val Ser Phe Gln Ser Asp Ile Gly Pro Tyr Gln Ser Gly
            35                  40                  45

Arg Phe Tyr Thr Lys Pro Pro Gln Cys Val Asp Ile Pro Ala Asp Leu
        50                  55                  60

Arg Leu Cys His Asn Val Gly Tyr Lys Lys Met Val Leu Pro Asn Leu
    65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
               100                 105                 110

Cys Ser Leu Phe Ala Pro Val Cys Leu Asp Arg Pro Ile Tyr Pro Cys
           115                 120                 125

Arg Trp Leu Cys Glu Ala Val Arg Asp Ser Cys Glu Pro Val Met Gln
       130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
               165                 170                 175

Ser Lys Pro Gln Gly Thr Thr Val Cys Pro Pro Cys Asp Asn Glu Leu
           180                 185                 190

Lys Ser Glu Ala Ile Ile Glu His Leu Cys Ala Ser Glu Phe Ala Leu
       195                 200                 205

Arg Met Lys Ile Lys Glu Val Lys Lys Glu Asn Gly Asp Lys Lys Ile
   210                 215                 220
```

```
Val Pro Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
                245                 250                 255

Cys His Gln Leu Asp Asn Leu Ser His His Phe Leu Ile Met Gly Arg
            260                 265                 270

Lys Val Lys Ser Gln Tyr Leu Leu Thr Ala Ile His Lys Trp Asp Lys
            275                 280                 285

Lys Asn Lys Glu Phe Lys Asn Phe Met Lys Lys Met Lys Asn His Glu
        290                 295                 300

Cys Pro Thr Phe Gln Ser Val Phe Lys
305                 310

<210> SEQ ID NO 3
<211> LENGTH: 240
<212> TYPE: DNA
<213> ORGANISM: Homo sapiens

<400> SEQUENCE: 3
aacagcctgc ctgtccccc gcactttta catatatttg tttcatttct gcagatggaa      60
agttgacatg ggtggggtgt ccccatccag cgagagagtt tcaaaagcaa aacatctctg  120
cagtttttcc caagtaccct gagatacttc ccaaagccct tatgtttaat cagcgatgta  180
tataagccag ttcacttaga caactttacc cttcttgtcc aatgtacagg aagtagttct  240
```